United States Patent [19]

Brancq et al.

[11] Patent Number: 5,508,454
[45] Date of Patent: Apr. 16, 1996

[54] QUATERNARY AMMONIUM DERIVATIVES, THE PROCESS FOR THEIR PREPARATION AND THEIR USE AS SURFACTANTS

[75] Inventors: Bernard Brancq, Chesnay; Jean-Pierre Boiteux, Saix, both of France

[73] Assignee: Societe D'Exploitation de Produits Pour les Industries Chimiques -SEPPIC, Paris, France

[21] Appl. No.: 285,930

[22] Filed: Aug. 4, 1994

[30] Foreign Application Priority Data

Jun. 28, 1994 [FR] France .................................. 94 07930

[51] Int. Cl.⁶ ................................................ C07C 231/00
[52] U.S. Cl. .................... 554/69; 554/52; 554/68
[58] Field of Search ..................... 554/52, 68, 69

[56] References Cited

U.S. PATENT DOCUMENTS 2,794,808  6/1957  Albrecht et al. ........................ 554/52

FOREIGN PATENT DOCUMENTS

| | | |
|---|---|---|
| 0302329 | 2/1989 | European Pat. Off. . |
| 1326561 | 8/1963 | France . |
| 1498579 | 9/1968 | France . |
| 1114516 | 5/1968 | United Kingdom . |
| 1234408 | 6/1971 | United Kingdom . |

OTHER PUBLICATIONS

Chemical Abstracts, vol. 63, No. 4, Aug. 16, 1965—abstract 4459d.
Chemical Abstracts, vol. 65, No. 12—Dec. 5, 1966.

*Primary Examiner*—José G. Dees
*Assistant Examiner*—Deborah D. Carr
*Attorney, Agent, or Firm*—Burgess, Ryan & Wayne

[57] ABSTRACT

The present invention relates to novel quaternary ammonium derivatives which have properties similar to those of non-ionic, amphoteric and cationic surfactants, to their preparation and to their use as surfactants in foaming and emulsifying compositions intended for use in the fields of pharmaceutics, cosmetics, hygiene and detergency.

These derivatives have the general formula

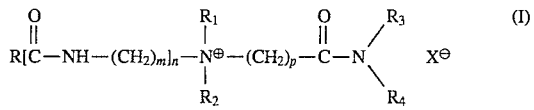

wherein essentially R is an alkyl or alkenyl radical having from 5 to 29 carbon atoms, $R_1$ and $R_2$ are an alkyl radical having from 1 to 4 carbon atoms, $R_3$ is a 2-hydroxyethyl, 2-hydroxypropyl, 3-hydroxypropyl, methyl or 2,3,4,5,6-pentahydroxyhexyl radical and X is a halogen atom or a hydroxyl group.

15 Claims, No Drawings

QUATERNARY AMMONIUM DERIVATIVES, THE PROCESS FOR THEIR PREPARATION AND THEIR USE AS SURFACTANTS

The present invention relates to novel quaternary ammonium derivatives, to the process for their preparation and to their use as surfactants.

The invention is applicable especially in the preparation of foaming, cleaning, emulsifying and conditioning compositions intended for use in the fields of pharmaceutics, cosmetics, hygiene, detergency and textiles.

It is known that to produce, at relatively low cost, foaming, cleaning, emulsifying or conditioning formulations simultaneously having good properties in terms of efficacy, protection and skin compatibility, it is currently necessary to combine different surfactants each having a particular activity and particular properties.

Thus, in general, a modern foaming or cleaning formulation comprises at least three different types of surfactant selected from the four major families of surfactants, namely the anionics, the amphoterics, the cationics and the nonionics.

The role of these known surfactants can be depicted in the following manner.

Anionic surfactants have good foaming properties and generally constitute the basic cleaning product.

Salified alkyl-ether-sulfates, salified alkylsulfates, salified α-olefinsulfonates and salified paraffinsulfonates, and mixtures thereof, may be mentioned as anionics in common use, especially in the fields of pharmaceutics, cosmetics, hygiene, detergency and textiles.

Sodium lauryl-ether-sulfate is particularly preferred among these anionics.

Amphoteric surfactants are generally cleaning products which make it possible to improve tolerance and foam stability.

Alkylbetaines, alkylamidobetaines, sultaines, imidazoline derivatives, phosphobetaines, amphopolyacetates and amphopropionates, and mixtures thereof, may be mentioned here as amphoteric surfactants in common use.

Cocamidopropylbetaine is particularly preferred among these amphoterics.

Non-ionic surfactants have solubilizing or emulsifying properties or in some cases (especially alkylpolyglucosides) thickening or foaming properties.

Hydrogenated castor oil, polysorbates, ethoxylated fatty alcohols, ethoxylated fatty acids, alkyl-polyglucosides and copra amides, and mixtures thereof, may be mentioned here as non-ionic surfactants.

Copra diethanolamide is particularly preferred among these nonionics, especially because of its super-fatting properties.

Cationic surfactants have an excellent "conditioning" effect, i.e. they make it possible to improve the suppleness and appearance of the hair, thereby making it easier to disentangle or style.

These products have weak cleaning or foaming properties. Moreover, their use causes a drop in foam stability. It is for this reason that they are generally associated with the simultaneous use of an amphoteric surfactant.

Cationic surfactants are used especially in disentangling balms and so-called "two-in-one" shampoos and sometimes for their emulsifying properties.

Quaternary ammonium derivatives, such as, in particular, cetyltriammonium chloride (CTAC) or dimethyldistearylammonium chloride (DMDSAC), may be mentioned as cationic surfactants in common use.

Cationic polymers may be used as an alternative.

A novel family of quaternary ammonium derivatives have been discovered, and it is this which forms the basis of the present invention, said derivatives simultaneously having the properties of amphoterics, nonionics land cationics and thus making it possible to produce foaming, cleaning, emulsifying or conditioning formulations containing a limited number of ingredients. In particular, the novel quaternary ammonium derivatives according to the present invention make it possible to produce binary foaming formulations which combine a compound of the invention with a known anionic.

The compounds according to the present invention have the following formula:

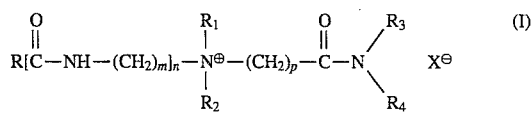

in which:

R is a linear or branched alkyl or alkenyl radical having from 5 to 29 carbon atoms;

m is an integer equal to 2 or 3;

n is an integer equal to 0 or 1;

$R_1$ and $R_2$ are independently:
an alkyl radical having from 1 to 4 carbon atoms, or
a hydroxymethyl, hydroxyethyl or hydroxypropyl radical;

p is an integer between 1 and 3;

$R_3$ is a group

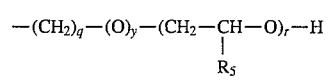

in which:

q is an integer between 1 and 5, y is an integer equal to 0 or 1, $R_5$ is a hydrogen atom or a methyl radical, and r is an integer between 0 and 10, it being specified that r and y cannot simultaneously be equal to 0;

a group

in which:

s is an integer between 0 and 2, t is an integer between 0 and 6, and u is an integer between 0 and 5;

or a group

in which:

v is an integer equal to 0 or 1, and w is an integer between 1 and 6;

$R_4$ is the hydrogen atom or has the same meaning as $R_3$; and X is a counterion, preferably a chlorine or bromine atom or a hydroxyl group.

In this definition, the expression "$R_4$ has the same meaning as $R_3$" has been used for reasons of simplicity and denotes that $R_4$ can be the same groups as those represented by $R_3$, without $R_3$ and $R_4$ necessarily being identical in this case.

In their applications, the compounds according to the present invention can be used in the pure form, but also as a mixture.

In fact, these compounds can be prepared from a pure fatty acid to give compounds in which the group R is a defined alkyl or alkenyl radical. They can also be prepared from a mixture of fatty acids of variable chain length to give a mixture of compounds of formula I which will differ in the nature of the radical R.

Tests performed within the framework of the present invention have shown that the compounds of formula I have properties comparable to those of amphoteric surfactants in terms of foaming and thickening power, to those of non-ionic surfactants in terms of thickening and superfatting power, and to those of cationic surfactants in terms of conditioning effect.

A first-preferred subfamily of compounds of the invention consists of the compounds of formula I in which n is equal to 0;

R is a linear or branched alkyl or alkenyl radical having from 8 to 18 carbon atoms, preferably selected from the group consisting of the following radicals:
$CH_3(CH_2)_7—$; $CH_3(CH_2)_9—$; $CH_3(CH_3)_{11}—$; $CH_3(CH_2)_{13}—$; $CH_3—(CH_2)_{15}—$; $CH_3(CH_2)_7—CH=CH—(CH_2)_8—$; $CH_2=CH—(CH_2)_9—$; and m, $R_1$, $R_2$, p, $R_3$ and $R_4$ are as defined above.

Another preferred subfamily of compounds of the invention consists of the compounds of formula I in which n is equal to 1;

R is a linear or branched alkyl or alkenyl radical having 7 to 17 carbon atoms, preferably selected from the group comprising the following radicals:
$CH_3(CH_2)_6—$; $CH_3(CH_2)_8—$; $CH_3(CH_2)_{10}—$; $CH_3(CH_2)_{12}—$; $CH_3(CH_2)_{14}—$; $CH_3(CH_2)_{16}—$; $CH_3(CH_2)_7—CH=CH—(CH_2)_7—$; $CH_3(CH_2)_5—CH=CH—(CH_2)_7—$; $CH_3(CH_2)_5—CHOH—CH_2—CH=CH—(CH_2)_7—$; $CH_3(CH_2)_4—CH=CH—CH_2—CH=CH—(CH_2)_7—$; $CH_3—(CH_2—CH=CH)_3—(CH_2)_7—$; $CH_2=CH—(CH_2)_8—$; and m, $R_1$, $R_2$, p, $R_3$ and $R_4$ are as defined above.

Among these two subfamilies, the particularly preferred compounds of formula I are those in which $R_3$ is a radical selected from the group consisting of 2-hydroxyethyl, 2-hydroxypropyl, 3-hydroxypropyl, methyl and 2,3,4,5,6-pentahydroxyhexyl radicals.

The compounds of formula I which are currently very particularly preferred within the framework of the present invention are those in which m is equal to 3;

n is equal to 1;

$R_1$ and $R_2$ are a methyl radical;

p is equal to 1;

$R_3$ is a 2-hydroxyethyl radical;

$R_4$ is the hydrogen atom;

X is a chlorine atom or a hydroxyl group; and

R is as defined above.

These compounds therefore have the formula $$R—\overset{O}{\overset{\|}{C}}—NH—(CH_2)_3—\overset{CH_3}{\underset{CH_3}{N^\oplus}}—CH_2—\overset{O}{\overset{\|}{C}}—N\diagup\!\!\!\!\diagdown\begin{array}{c}CH_2—CH_2OH\\H\end{array} \quad X^\ominus$$

Other preferred compounds of formula I are those in which n is equal to 0;

$R_1$ and $R_2$ are a methyl radical;

p is equal to 0;

$R_3$ is a 2-hydroxyethyl radical;

$R_4$ is the hydrogen atom or a 2-hydroxyethyl radical;

X is a chlorine atom or a hydroxyl group; and

R is as defined above.

According to a second feature, the object of the present patent application is to cover a process for the preparation of the quaternary ammonium derivatives of formula I given above.

In general terms, this process comprises: the amidation of an amine of the formula $$HN\diagup\!\!\!\!\diagdown\begin{array}{c}R_3\\R_4\end{array} \quad (II)$$

with a compound of the formula $$R[\overset{O}{\overset{\|}{C}}—NH—(CH_2)_m]_n—\overset{R_1}{\underset{R_2}{N^\oplus}}—(CH_2)_p—\overset{O}{\overset{\|}{C}}—Z \quad (III)$$

in which R, m, n, $R_1$, $R_2$ and p are as defined above; and Z is a group OH, $OCH_3$, $OC_2H_5$, $OC(O)CH_2Cl$, Cl or OM, where M is an alkali metal.

This step will be designated by "Step C" in the Examples.

According to one particular characteristic, the abovementioned compound of formula (III) is obtained by the quaternization of an amine of the formula $$R[\overset{O}{\overset{\|}{C}}—NH—(CH_2)_m]_n—N\diagup\!\!\!\!\diagdown\begin{array}{c}R_1\\R_2\end{array} \quad (IV)$$

in which R, m, n, $R_1$ and $R_2$ are as defined above, with a compound of the formula $$Cl—CH_2—CO—Z \quad (V)$$

in which Z is as defined above.

This step will be designated by "Step B" in the Examples.

According to another particular characteristic, within the framework of the preparation of the compounds of formula I in which n is equal 1, the compound of formula IV is obtained by the condensation of an aminoalkylamine of the formula $$NH_2—(CH_2)_m—N\diagup\!\!\!\!\diagdown\begin{array}{c}R_1\\R_2\end{array} \quad (VI)$$

in which m, $R_1$ and $R_2$ are as defined above, with a fatty acid of the formula RCOOH or a precursor thereof, such as its methyl ester or one of its glycerides, R being as defined above.

This step will be designated by "Step A" in the Examples.

The abovementioned amidation, quaternization and condensation reactions are conventional reactions and those skilled in the art may refer to the existing literature in order to determine the appropriate conditions (temperature, duration, nature of the solvents, etc.) for carrying out these reactions successfully.

It has been found, totally unexpectedly, that the color of the products of formula (I) can be considerably improved if the amidation of the amine of formula (II) with the compound of formula (III) is followed by a treatment with a compound selected from the group comprising acetic anhydride and acetyl chloride, so as to reduce the residual amount of amine to a value below 2%, preferably below 1%; it is this finding which constitutes a novel feature of the process of the present invention.

The conditions of this treatment may easily be determined by those skilled in the art.

According to a third feature, the object of the present patent application is to cover foaming, cleaning, emulsifying or conditioning compositions comprising at least one compound of formula (I) as defined above, in combination with an anionic surfactant in a weight ratio of between 99:1 and 1:99.

This anionic surfactant can be one of the commonly used anionics mentioned in the introduction of the present patent application. It will preferably be sodium lauryl-ether-sulfate.

Finally, according to a fourth feature, the object of the present patent application is to cover the use of the above-mentioned quaternary ammonium derivatives of formula (I) for the preparation of foaming, emulsifying, cleaning and conditioning compositions.

The following Examples, which are given without implying a limitation, will illustrate the present invention.

The percentages are expressed by weight in these Examples, unless indicated otherwise.

EXAMPLE 1

Example of the Preparation of a Compound According to the Invention

STEP A 24.2 kg of dimethylaminopropylamine are added to 45 kg of fatty acid in a general-purpose vat.

This fatty acid is actually a mixture of $C_{14}$, $C_{16}$ and $C_{18}$ acids of the following composition:

$C_{14}$: 2%

$C_{16}$: 45%

$C_{18}$: 53%

The resulting mixture is heated at 155° C. until the acid number drops below 5.

The excess dimethylaminopropylamine is then removed under reduced pressure to give 58.3 kg of amide.

STEP B 24.7 kg of the amide obtained in step A are dissolved in 55 kg of isopropyl alcohol.

This mixture is heated to 60° C. and 9.2 kg of sodium monochloroacetate are added, with stirring.

After stirring for 11 hours at 100° C., the whole is cooled to 60° C. and filtered.

STEP C 48.5 kg of the filtrate obtained in step B are heated under reduced pressure until the isopropyl alcohol has been removed.

3.3 kg of monoethanolamine are added to the resulting product.

After a reaction time of 6 hours at 155° C., 22 kg of a deep beige-colored solid are obtained.

The resulting product has the following characteristics:

Color (molten product): 11 Vcs

Free monoethanolamine: 0.25% pH (10%): 8.32

This product has the following structural formula:

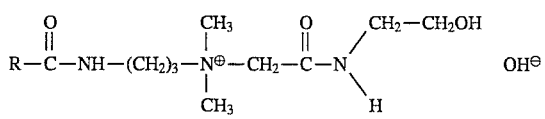

EXAMPLE 2

STEP A

Step A of Example 1 is repeated, the fatty acid being replaced with a mixture of the following composition:

$C_{10}$: 1%

$C_{12}$: 55%

$C_{14}$: 23%

$C_{16}$: 10%

$C_{18}$: 2%

$C_{18'}$: 8%

STEP B 22.5 kg of the alkylamidopropyldimethylamine prepared in step A are dissolved in 37 kg of isopropyl alcohol at 50° C.

After the addition of 9.5 kg of sodium monochloroacetate, the mixture is heated at 95° C. for 15 hours, with stirring, and then cooled to 50° C. and filtered.

STEP C 46.1 kg of the filtrate obtained in step B are heated under reduced pressure until the isopropyl alcohol has been removed.

After the addition of 3.0 kg of monoethanolamine, the reaction medium is heated to 170° C., with stirring, and kept at this temperature for 6 hours.

The resulting reaction mixture is diluted in water at about 60° C. to give 32.7 kg of a clear liquid containing 39.8% of solids and having the following characteristics:

Colour: 10 Vcs

Free monoethanolamine: 0.13% pH (product): 7.55

Viscosity at 20° C. : 1250 mPa.s

EXAMPLE 3

STEP B 25.4 kg of the alkylamidopropyldimethylamine prepared in step A of Example 2 and 3.9 kg of methyl alcohol are heated to 80° C., with stirring.

9.8 kg of methyl monochloroacetate are added over 1 hour and the resulting reaction mixture is kept at 80° C. for 6 hours.

STEP C 32 kg of the reaction mixture obtained in step B are heated to 60° C. and added over half an hour to a mixture, heated to 90° C., of 4 kg of monoethanolamine and 0.05 kg of sodium methylate as a 30% solution in methyl alcohol.

After a reaction time of 5 hours under vacuum at 100° C., the product obtained is cooled and diluted to a solids content of 41.3%.

The resulting clear liquid has the following characteristics:

Colour: 5 Vcs

Free monoethanolamine: 0.9% pH (5%): 5.9

Viscosity at 20° C. : 51 mPa.s

EXAMPLE 4

Influence of acetic anhydride on the color of the finished product

Steps A and B of Example 1 are repeated in order to prepare 62.5 kg of filtrate.

STEP C

The 62.5 kg of filtrate prepared in this way are heated under reduced pressure until the isopropyl alcohol has been totally removed.

3.5 kg of monoethanolamine are added to the resulting product.

After a reaction time of 3 hours at 150° C., the reaction medium is cooled to 70° C. and 0.6 kg of acetic anhydride is added.

After stirring for 3 hours at 70° C., 26.5 kg of a light beige-colored solid are obtained.

The product obtained has the following characteristics:

Color (molten product): 8 Vcs

Free monoethanolamine: 0.32% pH (10%): 7.75

This Example demonstrates the influence of acetic anhydride on the color of the finished product.

In fact, the color of the product prepared in Example 1 is 11 Vcs.

The product prepared under the same conditions with the addition of acetic anhydride in step C has a color of 8 Vcs, representing a fairly distinct improvement.

EXAMPLE 5

Influence of acetic anhydride on the color of the finished product

Steps A and B of Example 2 are repeated in order to prepare 52.0 kg of filtrate.

STEP C

The 52.0 kg of filtrate obtained in this way are heated under reduced pressure until the isopropyl alcohol has been totally removed.

After the addition of 3.2 kg of monoethanolamine, the reaction medium is stirred at 180° C. for 3 hours and then cooled to 70° C.; finally, 1.5 kg of acetic anhydride are added.

After a reaction time of 3 hours, the resulting crude product is diluted in water to give 50 kg of a liquid comprising 39% of solids and having the following characteristics:

Colour: 3 Vcs

Free monoethanolamine: 0.34% pH (product): 6.63

Viscosity at 20° C.: 1670 mPa.s

This Example demonstrates the influence of acetic anhydride on the color of the finished product.

In fact, the color of the product prepared in Example 2 is 10 Vcs.

The product prepared under the same conditions with the addition of acetic anhydride in step C has a color of 3 Vcs, representing a distinct improvement.

EXAMPLE 6

Preparation of a compound of the invention of formula (I) in which n=0

STEP B

In a glass reactor, 55 g of methyl monochloroacetate are added gradually to a refluxing solution of 495 g of alkyldimethylamine in 55 g of methanol.

The alkyl moiety of this dimethylamine has the following composition:

$C_8$: 4%

$C_{10}$: 6%

$C_{12}$: 52%

$C_{14}$: 18%

$C_{16}$: 10%

$C_{18}$: 10%

The reaction medium is refluxed for 4 hours and then cooled and filtered.

STEP C 578 g of the filtrate obtained in step B are heated to 60° C. under reduced pressure and added to a mixture, heated to 70° C., of 92 g of monoethanolamine and 5.3 g of sodium methylate as a 30% solution in methyl alcohol.

After a reaction time of 2 hours under vacuum at 85°–90° C., the resulting crude product is diluted in water to a solids content of 47.7%.

The resulting clear liquid has the following characteristics:

Color: 6 Vcs

Free monoethanolamine: 0.3% pH (10%): 5.5

Viscosity at 25° C.: 127 mPa.s

The resulting product has the following chemical structure:

$$R-\overset{\overset{\displaystyle CH_3}{|}}{\underset{\underset{\displaystyle CH_3}{|}}{N^{\oplus}}}-CH_2-\overset{\overset{\displaystyle O}{\|}}{C}-N\overset{\diagup CH_2CH_2OH}{\diagdown H} \quad Cl^{\ominus}$$

EXAMPLE 7

Example of the preparation of a compound according to the invention of formula (I) in which n=0

STEP B

Step A of Example 6 is repeated in order to prepare 578 g of filtrate.

STEP C

A methanolic solution of the 578 g of product obtained in step B is heated to 60° C. under reduced pressure and added to a mixture, heated to 70° C., of 156 g of diethanolamine and 6.0 g of sodium methylate as a 30% solution in methyl alcohol.

After a reaction time of 2 hours under vacuum at 85°–90° C., the resulting crude product is diluted in water to a solids content of 53.6%.

The resulting clear liquid has the following characteristics:

Color: 6 Vcs

Free diethanolamine: 1.66% pH (10%): 8.1

Viscosity at 25° C.: 63 mPa.s

The resulting product has the following chemical structure:

$$R-\overset{\overset{\displaystyle CH_3}{|}}{\underset{\underset{\displaystyle CH_3}{|}}{N^{\oplus}}}-CH_2-\overset{\overset{\displaystyle O}{\|}}{C}-N\overset{\diagup CH_2CH_2OH}{\diagdown CH_2CH_2OH} \quad Cl^{\ominus}$$

Demonstration of the Properties of the Compounds According to the Invention

The properties of the compounds according to the invention were compared with those of anionic, amphoteric, non-ionic and cationic surfactants in common use.

The following methods of determination were used for this purpose:

| PROPERTY | METHOD |
|---|---|
| Foam volume | ISO 696-1975 |
| Wetting powder | AFNOR NFT 73-406 |
| Solubilizing power IPM | Technical document PROTEOL K 25 ref. GL/0239/GB/01/January 93 |
| Disentangling power | KAMATH Y. K., WIGMANN H. D. Measurement of Combing Forces - J. Soc. Cosmet. Chem., 37, 3, 111–124, 1986 |
| Index of Substantivity to keratin | LUTZ D., HOLTZINGER G., KHAIAT A., Substantivity of Cationics to the Hair. A New Determination - Methodology - Cosmet. Toilet. Manufacture, 130–137, 1991/1992 |
| HET-CAM | INVITTOX HET-CAM TEST - INVITTOX PROTOCOL no. 47, January 1992 |
| Conditioning effect | Technical document PROTEOL VS 22 ref. GL/0113/GB/01/February 92 |

The results obtained have been summarized in Table 1.

These results show that the compounds according to the invention have properties comparable to those of amphoteric, non-ionic and cationic surfactants.

To confirm the value of the compounds according to the invention in the preparation of foaming and emulsifying compositions, the characteristics of a binary formulation incorporating a compound according to the invention and an anionic surfactant were compared with the following four compositions:

Composition A:

A binary composition incorporating an anionic surfactant and an amphoteric surfactant.

Composition B:

A ternary formulation incorporating an anionic surfactant, an amphoteric surfactant and a non-ionic surfactant.

Compositions C and D:

A four-component formulation incorporating an anionic surfactant, a non-ionic surfactant, an amphoteric surfactant and a cationic surfactant.

The results obtained have been collated in Table 2.

These results show that the binary formulation incorporating a compound according to the invention has properties comparable or even superior to those of four-component formulations such as the ones currently in existence, and very distinctly superior to those of two- or three-component formulations.

Composition A has a good cleaning effect but none of the conventional cosmetic properties.

Due to the presence of a non-ionic surfactant, composition B has a superfatting effect which improves the feel of the foam in particular.

Four-component composition C also has a good conditioning effect.

Four-component composition D has good properties but suffers the disadvantage of having a cloudy appearance.

The following abbreviations have been used in Tables 1 and 2:

NALES: Sodium lauryl-ether-sulfate

NALS: Sodium laurylsulfate ai: Active ingredient

SAS: Paraffinsulfonate

LAS: Dodecylbenzenesulfonate

CAPB: Cocamidopropylbetaine

DMDSAC: Dimethyldistearylammonium chloride phi: Initial pH

IPM: Isopropyl myristate sc: Solids content

CTAC: Cetyltriammonium chloride

TABLE 1

COMPARISON OF THE BASIC PROPERTIES OF SURFACTANTS

| | Anionic NALES | Amphoteric CAPB | Non-ionic (Copra amide) | Cationic DMDSAC | Invention Compound of Example 2 | Invention Compound of Example 1 |
|---|---|---|---|---|---|---|
| Foam volume 1% sc, 40° C., hard water + dirt | + | +++ | 0 | 0 | +++ | +/++ |
| Feel of foam | + | + | +++ | + | ++ | +++ |
| Wetting power 0.1% sc, 25° C., pHi | +++ | ++ | + | 0 | | +/++ |
| Solubilizing power IPM (μl/g of ai) | ++ | +/++ | not determinable | not determinable | +++ | not determinable |
| Disentangling power | 0 | 0 | 0 | +++ | ++ | +++ |
| Index of substantivity to keratin | 0 | 0 | 0 | +++ | +++ | +++ |
| Emulsifying power | 0 | 0 | + | + | + | ++ |
| HET-CAM | + | + | +++ | 0 | + | +++ |
| Thickening capacity | + | ++ | +++ | 0 | +++ | +++ |
| Solubility | +++ | +++ | + | + | ++ | + |
| Conditioning effect | 0 | + | + | +++ | +++ | +++ |

TABLE 2

COMPARISON OF DIFFERENT SHAMPOO FORMULATIONS

|  | A | B | C | D | Invention |
|---|---|---|---|---|---|
| NALES | 10% ai | 10% ai | 10% ai | 10% ai | 10% ai |
| Cocamidopropylbetaine | 3% ai | 2% ai | 2% ai | 2% ai | — |
| Copra diethanolamide |  | 1% ai | 1% ai | 1% ai | — |
| Compound of Example 2 |  |  |  |  | 3% ai |
| CTAC |  |  | 1% ai |  | — |
| Cationic polymer (Jaguar C13-5) |  |  |  | 0.5% ai | — |
| Appearance | c | c | c | cloudy | c |
| Viscosity (pH = 5) | 7500 (+1.6% NaCl) | 4300 (+1.5% NaCl) | 16500 (0% NaCl) | 4000 (1% NaCl) | 6000 (1.7% NaCl) |
| Foam, hard water + dirt | 450 ml (88%) | 490 ml (90%) | 483 ml (93%) | 483 ml (93%) | 470 ml (93%) |
| Superfatting effect on foam | + | ++ | +++ | ++++ | ++++ |
| Start of foaming | ++ | ++ | ++ | +++ | ++++ |
| Softness | ++ | ++ | +++ | ++++ | ++++ |
| Shine | ++ | ++ | ++ | ++ | +++ |
| Volume  Hair | +++ | +++ | ++ | ++ | ++ |
| Suppleness | ++ | ++ | ++ | +++ | +++ |
| Static electricity | + | + | ++ | +++ | +++ |
| Ease of combing | ++ | ++ | ++ | +++ | ++++ |

+ poor
++ moderate
+++ good
++++ excellent
c: clear

Complementary tests showed that the compounds according to the invention have anti-irritant properties towards the anionic surfactants in conventional use, without in any way degrading the foaming power.

The compounds according to the invention therefore have an advantage over the ethoxylated non-ionic compounds generally used for reducing the irritant properties of anionic surfactants, insofar as these non-ionic compounds cause a degradation of the foaming power.

Finally, it was demonstrated that the compounds according to the present invention have valuable emulsifying properties, especially for the formulation of hair balms or conventional emulsions. In this case, the compounds of the invention act as both a disentangling agent and an emulsifier.

A few Examples of formulations incorporating the compounds according to the present invention are now given below.

These formulations will be applicable especially in the fields of cosmetics, pharmaceutics (antiseptic liquid soap) and hygiene or else in the field of detergency (product for household or industrial use).

| Mild baby shampoo: | |
|---|---|
| NALES 2.2 EO | 6% ai |
| COMPOUND OF EXAMPLE 2 | 1.5% ai |
| Preservative | qs |
| Perfume | qs |
| Water | qsp 100 |

This shampoo does not sting the eyes or entangle the hair.

| Conditioning shampoo for damaged hair: | |
|---|---|
| NALES 2.2 EO | 9% ai |
| COMPOUND OF EXAMPLE 3 | 3% ai |
| Preservative | qs |
| Perfume | qs |
| Water | qsp 100 |
| NaCl | qs viscosity |

| Disentangling cream: | |
|---|---|
| COMPOUND OF EXAMPLE 1 | 2% ai |
| MONTANOV 68 ® | 1% ai |
| Diemthicone | 2% |
| Preservative | qs |
| Perfume | qs |
| Water | qsp 100 |

| Conditioner for dry ends: | |
|---|---|
| COMPOUND OF EXAMPLE 1 | 2% ai |
| Cyclomethicone | 5% |
| ACRYSOL 44 ® | 2% |
| Preservative | qs |
| Perfume | qs |
| Water | qsp 100 |

| Pearlescent liquid soap: | |
|---|---|
| NALES 2.2 EO | 7% ai |
| COMPOUND OF EXAMPLE 2 | 2% ai |
| Glycol stearate | 2% |
| Preservative | qs |
| Perfume | qs |
| Water | qsp 100 |
| NaCl | qs viscosity |

| 2-in-1 shampoo: | |
|---|---|
| NALES 2.2 EO | 12% ai |
| COMPOUND OF EXAMPLE 2 | 2% ai |
| COMPOUND OF EXAMPLE 1 | 0.5% ai |
| Glycol stearate | 2% |
| Dimethicone 50 cps | 1% |
| Preservative | qs |
| Perfume | qs |
| Water | qsp 100 |
| NaCl | qs viscosity |

| Permanent waving product (lotion): | |
|---|---|
| COMPOUND OF EXAMPLE 2 | 1% ai |
| COMPOUND OF EXAMPLE 1 | 2% ai |
| Ammonium thioglycolate | 8% |
| 70% sodium hydroxide solution | 10% |
| 28% aqueous ammonia | 3% |
| Thickener | 1% |

| | |
|---|---|
| Water | qsp 100 |

Shower gel:

| | |
|---|---|
| NALES 2.2 EO | 13% ai |
| COMPOUND OF EXAMPLE 3 | 2% ai |
| Preservative | qs |
| Perfume | qs |
| Water | qsp 100 |
| NaCl | qs viscosity |

2-in-1 shower gel:

| | |
|---|---|
| LANOL 84D ® | 2% |
| COMPOUND OF EXAMPLE 1 | 2% ai |
| NALES 2.2 EO | 15% ai |
| Opacifier | 0.5% |
| Preservative | qs |
| Perfume | qs |
| Water | qsp 100 |
| NaCl | qs viscosity |

Antiseptic liquid soap:

| | |
|---|---|
| COMPOUND OF EXAMPLE 2 | 8% |
| Chlorhexidine digluconate (20% solution) | 2.5% |
| Perfume | qs |
| Water | qsp 100 |

It should be noted that, in this formulation, the compound of the invention is not associated with an anionic surfactant. Unexpectedly, the activity of the chlorhexidine digluconate (which is of cationic character) is not degraded, despite the absence of an anionic surfactant.

Hand cream:

| | |
|---|---|
| MONTANOV 68 ® | 5% |
| COMPOUND OF EXAMPLE 1 | 0.5% ai |
| Paraffin oil | 15% |
| Glycerol | 5% |
| Water | qsp 100 |
| Perfume | qs |
| Preservative | qs |

Soothing body milk:

| | |
|---|---|
| MONTANOV 94 ® | |
| COMPOUND OF EXAMPLE 1 | 2% ai |
| LANOL 2681 ® | 10% |
| Water | qsp 100 |
| SEPIGEL 305 ® | 0.8% |
| Perfume | qs |
| Preservative | qs |

Moisturizing foam bath:

| | |
|---|---|
| NALES 2.2 EO | 15% ai |
| NALS | 5% ai |
| COMPOUND OF EXAMPLE 2 | 5% |
| Glycol stearate | 2% |
| Water | qsp 100 |
| Perfume | qs |
| Preservative | qs |
| NaCl | qs viscosity |

Textile softener (household use):

| | |
|---|---|
| COMPOUND OF EXAMPLE 1 | 4% |
| LANOL CTO wax ® | 1% |
| Preservative | qs |
| Perfume | qs |
| Water | qsp 100 |
| Citric acid | qs pH 3 |

Textile softener (industrial use):

| | |
|---|---|
| COMPOUND OF EXAMPLE 1 | 3% |
| MONTANOV 68 ® | 0.5% |
| Water | qsp 100 |

Dishwashing liquid:

| | |
|---|---|
| NALES 2.2 EO | 15% ai |
| SAS or LAS | 15% ai |
| COMPOUND OF EXAMPLE 2 | 3% ai |
| Perfume | qs |
| Preservative | qs |
| Water | qsp 100 |

Dishwashing liquid (for sensitive skin):

| | |
|---|---|
| NALES 2.2 EO | 20% ai |
| COMPOUND OF EXAMPLE 2 | 5% ai |
| Perfume | qs |
| Preservative | qs |
| Water | qsp 100 |

Lavatory descaling gel:

| | |
|---|---|
| COMPOUND OF EXAMPLE 2 | 2% |
| ACRYSOL 44 ® | 5% |
| Acetic acid | 5% |
| Color | qs |
| Perfume | qs |
| Water | qsp 100 |
| Citric acid | qs pH 3 |

In these formulations, the products mentioned by their tradenames correspond to the following products:

MONTANOV 68®: Cetearyl glucoside
ACRYSOL 44®: Urethane/C1–20 alkyl PEG copolymer
LANOL 84D®: Dioctyl malate
LANOL 2681®: Coconut caprylate/caprate
SEPIGEL 305®: Polyacrylamide and C12–14 isoparaffin laureth-7
Lanol CTO wax®: Cetearyl alcohol and ceteareth-33

What is claimed is:

1. A novel quaternary ammonium compound of the formula:

$$R[C(=O)-NH-(CH_2)_m]_n-\overset{R_1}{\underset{R_2}{N^\oplus}}-(CH_2)_p-C(=O)-N\begin{subarray}{l}R_3\\R_4\end{subarray}\ X^\ominus \quad (I)$$

in which:

R is a linear or branched alkyl or alkenyl radical having from 5 to 29 carbon atoms;

m is an integer equal to 2 or 3;

n is equal to 1;

$R_1$ and $R_2$ are independently:
an alkyl radical having from 1 to 4 carbon atoms, or a hydroxymethyl, hydroxyethyl or hydroxypropyl radical;

p is an integer between 1 and 3;

$R_3$ is a group $$-(CH_2)_q-(O)_y-(CH_2-\underset{R_5}{CH}-O)_r H$$

in which:

q is an integer between 1 and 5, y is an integer equal to 0 or 1, $R_5$ is a hydrogen atom or a methyl radical, and r is an integer between 0 and 10, it being specified that r and y cannot simultaneously be equal to 0;

a group $$-(CH_2)_s-(CHOH)_t-(CH_2)_u-CH_3$$

in which:

s is an integer between 0 and 2, t is an integer between 1 and 6, and u is an integer between 0 and 5;

or a group $$-(CH_2)_v-(CHOH)_w-CH_2OH$$

in which:

v is an integer equal to 0 or 1, and w is an integer between 1 and 6;

$R_4$ is the hydrogen atom or has the same meaning as $R_3$; and X is a chlorine or bromine atom or a hydroxyl group.

2. A quaternary ammonium compound of formula I according to claim 1 in which R is a linear or branched alkyl or alkenyl radical having 7 to 17 carbon atoms, selected from the group consisting of the following radicals:

$CH_3(CH_2)_6-$; $CH_3(CH_2)_8-$; $CH_3(CH_2)_{10}-$; $CH_3(CH_2)_{12}-$; $CH_3(CH_2)_{14}-$; $CH_3(CH_2)_{16}-$; $CH_3(CH_2)_7-CH=CH-(CH_2)_7-$; $CH_3(CH_2)_5-CH=CH-(CH_2)_7-$; $CH_3(CH_2)_5-CHOH-CH_2-CH=CH-(CH_2)_7-$; $CH_3(CH_2)_4-CH=CH-CH_2-CH=CH-(CH_2)_7-$; $CH_3(CH_2-CH=CH)_3-(CH_2)_7-$; and $CH_2=CH-(CH_2)_8-$; and m, $R_1$, $R_2$, p, $R_3$ and $R_4$ are as defined in claim 1.

3. A quaternary ammonium compound of formula I according to claim 1 in which $R_3$ is a radical selected from the group consisting of 2-hydroxyethyl, 2hydroxypropyl, 3-hydroxypropyl, and 2,3,4,5,6-pentahydroxyhexyl radicals.

4. A process for the preparation of the quaternary ammonium compounds of formula I according to claim 1, which comprises: the amidation of an amine of the formula

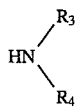 (II)

with a compound of the formula

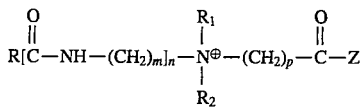 (III)

in which R, m, n, $R_1$, $R_2$, $R_3$ and p are as defined in claim 1; $R_4$ is hydrogen or $R_3$; and Z is selected from the group consisting of OH, OM, $OCH_3$, $OC_2H_5$, $OC(O)CH_2Cl$ and Cl, where M is an alkali metal.

5. A process according to claim 4 wherein the compound of Formula (III) is obtained by the quaternization of an amine of the formula

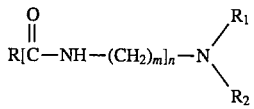 (IV)

with a compound of the formula

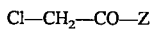 (v)

$$Cl-CH_2-CO-Z$$

in which R, m, n, $R_1$, $R_2$ and Z are as defined therein.

6. A process according to claim 16 wherein the compound of Formula (IV) is obtained by the condensation of an aminoalkylamine of the formula

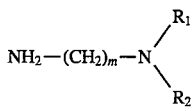 (VI)

in which m, $R_1$ and $R_2$ are as defined therein, with a fatty acid of the formula RCOOH or a precursor thereof, wherein R is a linear or branched alkyl or alkenyl radical having from 5 to 29 carbon atoms.

7. The process of claim 8 wherein the amount of residual amine is reduced to a value below 1%.

8. A process according to claim 4 wherein, in order to improve the color of the product of formula (I), the amidation of the amine of formula (II) with the quaternary ammonium derivative of formula (III) is followed by a treatment with a compound selected from the group consisting of acetic anhydride and acetyl chloride, so as to reduce the amount of residual amine to a value below 2%.

9. A foaming, cleaning, emulsifying or conditioning composition which comprises at least one compound of formula (I) as defined claim 1, in combination with an anionic surfactant in a weight ratio of between 99:1 and 1:99.

10. A composition according to claim 9, wherein said anionic surfactant is sodium lauryl-ether-sulfate.

11. A novel quaternary ammonium compound of the formula:

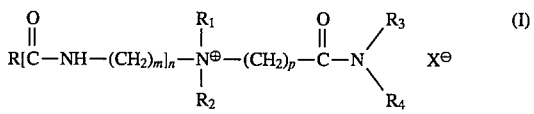 (I)

in which; R is a linear or branched alkyl or alkenyl radical having from 5 to 29 carbon atoms; m is an integer equal to 2 or 3; n is equal to 1; $R_1$ and $R_2$ are independently:

an alkyl radical having from 1 to 4 carbon atoms, or a hydroxymethyl, hydroxyethyl or hydroxypropyl radical;

p is an integer between 1 and 3; $R_3$ is a radical selected from the group consisting of 2-hydroxyethyl, 2-hydroxypropyl, 3-hydroxypropyl and 2,3,4,5,6-pentahydroxyhexyl radicals; $R_4$ is the hydrogen atom or has the same meaning as $R_3$; and X is a chlorine or bromine atom or a hydroxyl group.

12. A quaternary ammonium compound of the formula:

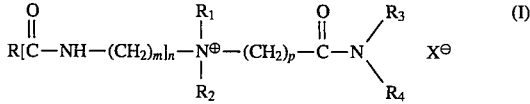 (I)

in which n is equal to 1; R is a linear or branched alkyl or alkenyl radical having 5 to 29 carbon atoms; m is equal to 3; $R_1$ and $R_2$ are a methyl radical; p is equal to 1; $R_3$ is a 2-hydroxyethyl radical; $R_4$ is the hydrogen atom; and X is a chlorine atom or a hydroxyl group.

13. A quaternary ammonium compound of formula:

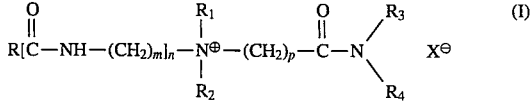 (I)

in which R is a linear or branched alkyl or alkenyl radical having from 5 to 29 carbon atoms; m is equal to 3; $R_1$ and $R_2$ are a methyl radical; p is equal to 1; R3 is a 2-hydroxyethyl radical; $R_4$ is a 2-hydroxyethyl radical and X is a chlorine atom or a hydroxyl group.

14. A quaternary ammonium compound of the formula:

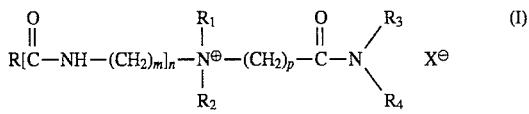

in which n is equal to 1, R is a linear or branched alkyl or alkenyl radical having 5 to 29 carbon atoms, m is equal to 3, $R_1$ and $R_2$ are independently an alkyl radical having from 1 to 4 carbon atoms, p is equal to 1, $R_3$ is a 2-hydroxyethyl radical, $R_4$ is a hydrogen atom, and X is a chlorine atom or a hydroxyl group.

15. A quaternary ammonium compound of the formula:

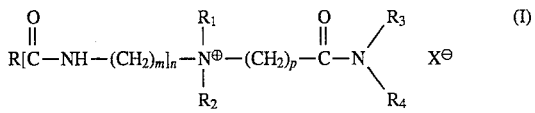

in which n is equal to 1, R is a linear or branched alkyl or alkenyl radical having 5 to 29 carbon atoms, m is equal to 3, $R_1$ and $R_2$ are independently an alkyl radical having form 1 to 4 carbon atoms, p is equal to 1, $R_3$ is a 2-hydroxyethyl radical, $R_4$ is a 2-hydroxyethyl radical, and X is a chlorine atom or a hydroxyl group.

* * * * *